United States Patent
Rajewski et al.

(10) Patent No.: US 6,562,952 B1
(45) Date of Patent: May 13, 2003

(54) PRECIPITATION OF PROTEINS FROM ORGANIC SOLUTIONS

(75) Inventors: Roger A. Rajewski, Lawrence, KS (US); Bala Subramaniam, Lawrence, KS (US); William K. Snavely, Lawrence, KS (US); Fenghui Niu, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 09/703,221

(22) Filed: Oct. 31, 2000

(51) Int. Cl.[7] .............................. A23J 1/00; A61K 9/14; A61L 9/04; B01D 61/00
(52) U.S. Cl. ................ 530/418; 530/419; 530/422; 530/424; 530/426; 530/427; 424/44; 424/45; 424/489; 210/651; 210/666; 210/710; 210/711
(58) Field of Search ................... 530/418, 419, 530/422, 424, 426, 427; 424/44, 45, 489; 210/651, 666, 710, 711

(56) References Cited

U.S. PATENT DOCUMENTS

| 5,770,559 | A | * | 6/1998 | Manning et al. ............... 514/2 |
| 5,833,891 | A | | 11/1998 | Subramaniam et al. ......... 264/7 |
| 5,874,029 | A | | 2/1999 | Subramaniam et al. ....... 264/12 |
| 5,916,585 | A | | 6/1999 | Cook et al. .................. 424/426 |
| 6,063,910 | A | * | 5/2000 | Debenedetti et al. ........ 530/418 |
| 6,113,795 | A | * | 9/2000 | Subramaniam et al. ..... 210/651 |

OTHER PUBLICATIONS

Yeo et al.; Formation of Microparticulate Protein Powders Using a Supercritical Fluid Antisolvent, *Biotechnology and Bioengineering*, 41:341–345 (1993).
Winters et al.; Precipitation of Proteins in Supercritical Carbon Dioxide; *J. Pharmaceutical Sciences*, 85(6):586–594 (1996).

* cited by examiner

Primary Examiner—Christopher S. F. Low
Assistant Examiner—Abdel A. Mohamed
(74) Attorney, Agent, or Firm—Hovey Williams LLP

(57) ABSTRACT

A process for forming small micron-sized (1-10 $\mu$m) protein particles is provided wherein a protein, a solvent system for the protein and an antisolvent for the protein solvent system are contacted under conditions to at least partially dissolve the protein solvent system in the antisolvent, thereby causing precipitation of the protein. The solvent system is made up of at least in part of a halogenated organic alcohol, most preferably 1,1,1,3,3,3-hexafluoro-2-propanol (HFIP). Preferably, a solution of the protein in the solvent system is sprayed through a nozzle into a precipitation zone containing the antisolvent (preferably $CO_2$) under near- or supercritical conditions.

16 Claims, 5 Drawing Sheets

PRECIPITATION OF PROTEINS FROM ORGANIC SOLUTIONS

BACKGROUND OF THE INVENTION

1. Field of the Invention

The present invention is broadly concerned with improved methods for the forming and precipitation of small protein or peptide particles making use of the precipitation using compressed antisolvents (PCA) process. More particularly, the invention is concerned with such a method and the resulting proteinaceous particles wherein the process is carried out using a halogenated organic alcohol as at least a part of the protein solvent; in particularly preferred forms, the solvent is 1,1,1,3,3,3-hexafluoro-2-propanol (HFIP), and the process yields micron-sized particles suitable for pharmaceutical uses without substantially degrading the protein.

2. Description of the Prior Art

Micron-sized (1–10 $\mu$m) protein particles are often deemed necessary for drug delivery systems such as controlled release and direct aerosol delivery to the lungs. Consistent commercial production of small protein particles of this type can be difficult. For example, spray drying techniques often lead to thermal denaturation of the protein, while milling and similar processes yield unacceptably broad size distributions and/or denaturation. Lyophilization can give particles in the desired size range, but with a broad distribution and/or denaturation; moreover, not all proteins of interest can be lyophilized to stable products.

In an effort to overcome these problems, supercritical fluid precipitation processes have been employed. Two processes that use supercritical fluids for particle formation are: (1) Rapid Expansion of Supercritical Solutions (RESS) (Tom, J. W. Debenedetti, P. G., 1991, *The Formation of Bioerodible Polymeric Microspheres and Microparticles by Rapid Expansion of Supercritical Solutions*. BioTechnol. Prog. 7:403–411), and (2) Gas Anti-Solvent (GAS) Recrystallization (Gallagher, P. M., Coffey, M. P., Krukonis, V. J., and Klasutis, N., 1989, *Gas Antisolvent Recrystallization: New Process to Recrystallize Compounds in Soluble and Supercritical Fluids*. Am. Chem. Sypm. Ser., No. 406; U.S. Pat. No. 5,360,478 to Krukonis et al.; U.S. Pat. No. 5,389,263 to Gallagher et al.). See also, PCT Publication WO 95/01221 and U.S. Pat. No. 5,043,280 which describe additional SCF particle-forming techniques.

In the RESS process, a solute (from which the particles are formed) is first solubilized in supercritical $CO_2$ to form a solution. The solution is then sprayed through a nozzle into a lower pressure gaseous medium. Expansion of the solution across this nozzle at supersonic velocities causes rapid depressurization of the solution. This rapid expansion and reduction in $CO_2$ density and solvent power leads to supersaturation of the solution and subsequent recrystallization of virtually contaminant-free particles. The RESS process, however, is not suited for particle formation from polar compounds because such compounds, which include drugs, exhibit little solubility in supercritical $CO_2$. Cosolvents (e.g., methanol) may be added to $CO_2$ to enhance solubility of polar compounds; this, however, affects product purity and the otherwise environmentally benign nature of the RESS process. The RESS process also suffers from operational and scale-up problems associated with nozzle plugging due to particle accumulation in the nozzle and to freezing of $CO_2$ caused by the Joule-Thompson effect accompanying the large pressure drop.

The relatively low solubilities of pharmaceutical compounds in unmodified carbon dioxide are exploited in the second process wherein the solute of interest (typically a drug, polymer or both) is dissolved in a conventional solvent to form a solution. The preferred ternary phase behavior is such that the solute is virtually insoluble in dense carbon dioxide while the solvent is completely miscible with dense carbon dioxide at the recrystallization temperature and pressure. The solute is recrystallized from solution in one of two ways. In the first method, a batch of the solution is expanded several-fold by mixing with dense carbon dioxide in a vessel. Because the carbon dioxide-expanded solvent has a lower solvent strength than the pure solvent, the mixture becomes supersaturated forcing the solute to precipitate or crystallize as microparticles. This process was termed Gas Antisolvent (GAS) recrystallization (Gallagher et al., 1989).

The second method involves spraying the solution through a nozzle into compressed carbon dioxide as fine droplets. In this process, a solute of interest (typically a drug, polymer or both) that is in solution or is dissolved in a conventional solvent to form a solution is sprayed, typically through conventional spray nozzles, such as an orifice or capillary tube(s), into supercritical $CO_2$ which diffuses into the spray droplets causing expansion of the solvent. Because the $CO_2$-expanded solvent has a lower solubilizing capacity than pure solvent, the mixture can become highly supersaturated and the solute is forced to precipitate or crystallize. This process has been termed in general as Precipitation with a Compressed Fluid Antisolvent (PCA) (Dixon, D. J.; Johnston, K. P.; Bodmeier, R. A. *AIChE J.* 1993, 39, 127–139.) and employs either liquid or supercritical carbon dioxide as the antisolvent. When using a supercritical antisolvent, the spray process has been termed Supercritical Antisolvent (SAS) Process (Yeo, S.-D.; Debenedetti, P. G.; Radosz, M.; Schmidt, H.-W. *Macromolecules* 1993, 26, 6207–6210.) or Aerosol Spray Extraction System (ASES) Müller, B. W.; Fischer, W.; Verfahren zur Herstellung einer mindestens einen Wirkstoff und einen Träger umfassenden Zubereitung, German Patent Appl. No. DE 3744329 A1 1989).

U.S. Pat. No. 6,063,910 describes a specific process for the production of protein particles by supercritical fluid precipitation. In this process, a solution of protein is prepared using a variety of solvents such as ethanol, DMSO and glycols, whereupon the solution is sprayed through a nozzle into an antisolvent under supercritical conditions, thereby effecting precipitation of the protein as small micron-sized products. In the case of insulin, the process was found to create a substantial loss of α-helicity and a marked increased in β-sheet and β-reverse turn content. (Winters et al., *J. Pharmaceutical Sciences*, 85(6):586–594 (1996)). The solvents used in the process of the '910 patent, and particularly DMSO, are not favored for pharmaceutical uses. For example, many such solvents leave a residuum in the precipitated particles, causing purity problems.

There is accordingly a real and unsatisfied need in the art for an improved protein precipitation process which avoids the solvent problems of many prior techniques while giving micron-sized particles of small size distribution and with little protein degradation.

SUMMARY OF THE INVENTION

The present invention overcomes the problems outlined above and provides an improved method for forming small protein particles of micron size, preferably from about 1–10 $\mu$m, and more preferably from about 1–5 $\mu$m. Broadly speaking, the process involves contacting a protein, a protein solvent system and an antisolvent for the protein solvent system under conditions to at least partially dissolve the protein solvent system in the antisolvent with consequent precipitation of the protein; the protein solvent system includes at least in part a halogenated organic alcohol, and preferably consists essentially of a single halogenated organic alcohol. Use of such solvents materially improves precipitation processes heretofore used and avoids many of the problems of the prior art.

A wide variety of solvent/antisolvent precipitation processes can be used in accordance with the invention. For example, the GAS and PCA processes can be employed. Preferably however, the solvents of the invention are used in the PCA process wherein the protein is first dissolved in the solvent system, and then droplets of the solution are sprayed into an antisolvent under conditions to precipitate protein particles.

The preferred halogenated organic alcohols are the halogenated alkyl alcohols, especially the $C_1$–$C_4$ alcohols. Particular alcohol solvents are HFIP, trifluoroethanol, 2-chloroethanol and mixtures thereof. The single most preferred solvent is HFIP (CAS #920-66-1). This solvent has a boiling point of 59° C. and a density of 1.618 g/ml, and is very soluble in $CO_2$. Normally, only a single halogenated organic alcohol will be used as a protein solvent. However, multiple-component solvent systems can also be employed, so long as such systems include a halogenated organic alcohol as at least a part thereof.

A variety of antisolvents can also be used in the invention, such as $CO_2$, propane, butane, isobutane, nitrous oxide, sulfur hexafluoride, trifluoromethane, hydrogen and mixtures thereof. $CO_2$ is the most preferred antisolvent, owing to its low cost, ready availability and critical properties ($T_c$=81.0° C. and $P_c$=73.8 bar or 1070 psi). Furthermore, $CO_2$ is non-toxic, non-flammable, recyclable, and "generally regarded as safe" by the FDA and pharmaceutical industry.

During processing, the contact between the protein solution system and antisolvent is carried out at near or supercritical conditions for the antisolvent, e.g., from about 0.5–2 $P_c$ and more preferably from about 0.9–1.5 $P_c$; when $CO_2$ is used as the antisolvent, pressure conditions are normally maintained at a level of from about 1000–2000 psig, and more preferably from about 1100–1600 psig. The temperature conditions during processing are generally relatively low in order to avoid heat denaturation of the protein. Generally, temperatures of up to about 60° C. and more preferably up to about 50° C. are used. When $CO_2$ is the antisolvent, such temperatures exceed the $T_c$.

In order to maximize production rates, the preferred process is carried out in a pressurized precipitation chamber equipped with a nozzle. The protein solution is sprayed through the nozzle into a precipitation zone containing the antisolvent. The resultant protein particles are collected in a downstream recovery filter, and can easily be further processed for pharmaceutical uses.

In most instances, the starting protein is dissolved in a halogenated organic alcohol solvent or solvent system containing such an alcohol, thereby producing true solutions. However, the invention is not so limited. That is, it is possible that the protein may be only partially dissolved or dispersed within the solvent. Therefore, as used herein, "solution" should be understood to mean not only true solutions but also partial solutions and dispersions. Similarly, while complete proteins are often processed in accordance with the invention, protein fragments or peptides could also be treated. Accordingly, the term "protein" refers to all types of proteinaceous species.

DETAILED DESCRIPTION OF THE PREFERRED EMBODIMENTS

The following examples set forth preferred techniques for the micronization of representative proteins, and the characterization of these proteins. It is to be understood, however, that these examples are provided by way of illustration and nothing therein should be taken as a limitation upon the overall scope of the invention.

EXAMPLE 1

In this example a series of biosynthetic insulin samples (Eli Lilly Lot No. 009LX9) dissolved in 20 mL HFIP were sprayed through an ultrasonic nozzle into supercritical $CO_2$ within a precipitation chamber using the techniques of the invention. The precipitated products were then tested to confirm that the final insulin products were not materially altered, as compared with the starting insulin samples.

Figures 1, 2:
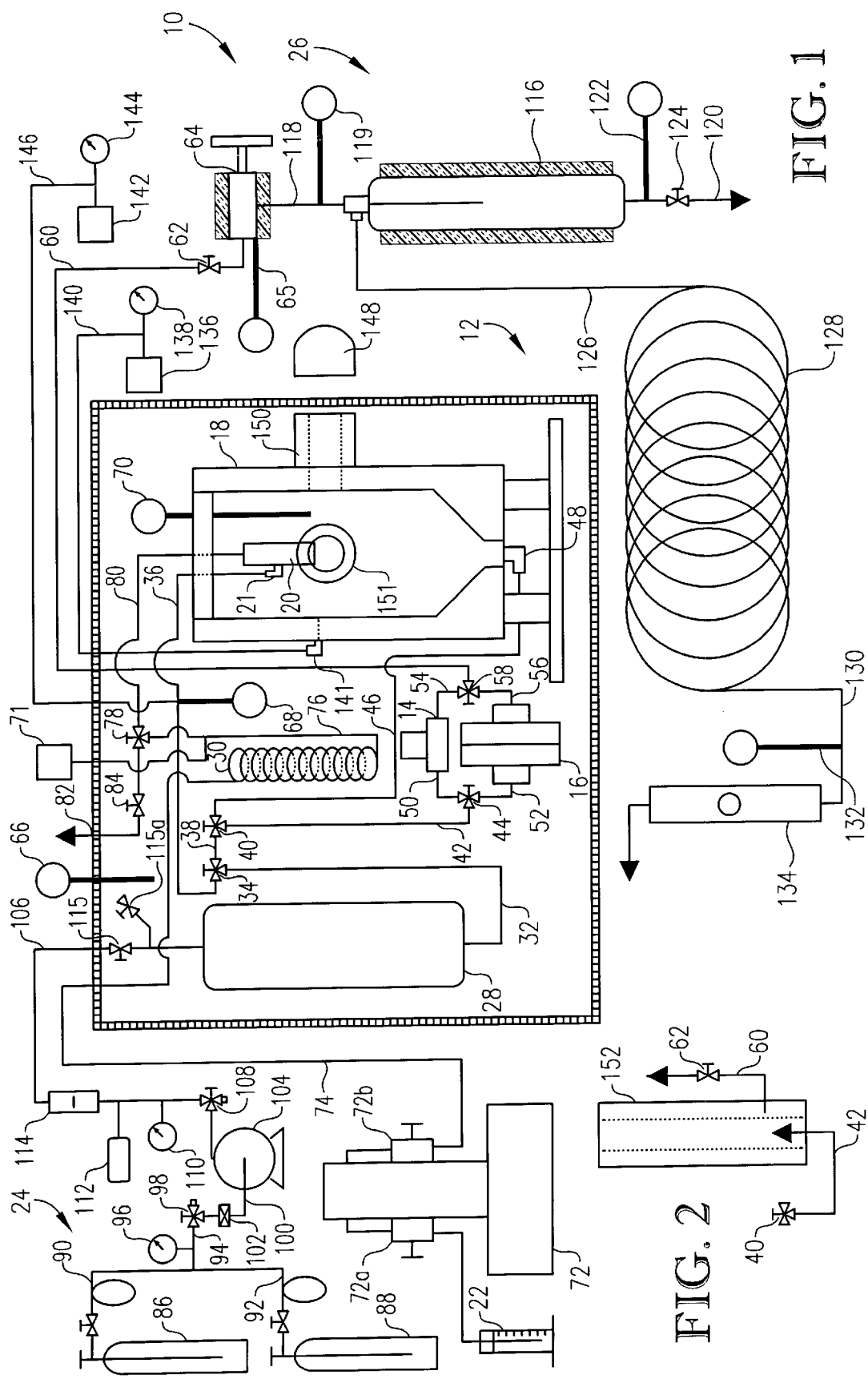
FIG. 1 is a schematic representation of preferred apparatus used in the precipitation of proteins in accordance with the invention.
FIG. 2 is a fragmentary schematic representation which, when viewed in connection with FIG. 1, depicts an alternative filtration apparatus.

The apparatus employed in this example is set forth in FIG. 1. Broadly speaking, the apparatus 10 included a temperature-controlled water bath 12 including therein a pair of interconnected filters 14, 16 and a precipitation chamber 18 equipped with an ultrasonic nozzle (Misonix Sonimist 600-1) 20 having a solution input 80. A protein-containing solution to be micronized is contained within a reservoir 22 and is directed through the nozzle 20 along with carbon dioxide from a supply 24. Protein particles from the chamber 18 are recovered in a recovery system 16.

In more detail, the heater for the water bath 12 is preferably a Fisher Scientific Allied Model 70 immersion heater (1000 W). A surge tank 28 (Whitey 304L-HDF4-2250CC) having a 2250 $cm^3$ capacity and a 1800 psig pressure rating is located within the bath 12, along with a coil of 1/16 inch stainless steel tubing 30, the filters 14, 16, and chamber 18. A conduit 32 leads from the bottom of tank 28 to a three-way valve 34. A first conduit 36 extends from an output of valve 34 to an inlet 21 of the nozzle 20. A second conduit 38 extends from the other output of valve 34 to another three-way valve 40. A first conduit 42 from the valve 40 is directed to three-way valve 44, whereas a second conduit 46 leads to the outlet 48 of chamber 18.

One conduit 50 of the valve 44 leads to the input of filter 14, whereas the second conduit 52 leads to the input of filter 16. The output conduits 54, 56 from the filters 14, 16 are connected to a three-way valve 58. The third conduit 60 from the valve 58 is equipped with a two-way valve 62 and leads to a heated micrometering valve 64 (Autoclave Engineers 30VRMM 4812) equipped with a thermocouple 65. As shown, the bath 12 is also provided with three thermocouples 66, 68 and 70, with the latter extending into chamber 18, as well as a pressure transducer 71.

The solution reservoir 22 is coupled with a syringe pump 72 (Isco 260D) having inlet and outlet valves 72a, 72b, with the latter having an output conduit 74 leading into bath 12 and particularly to the inlet side of coil 30. The outlet of coil 30 is connected to a conduit 76 coupled with transducer 71 and leading to a three-way valve 78; one output leg 80 from the valve 78 leads to the solution inlet of nozzle 20. The other output leg 82 is equipped with a two-way valve 84 and leads to the atmosphere.

The $CO_2$ supply 24 includes a pair of $CO_2$ tanks 86, 88 with valved outputs 90, 92 leading to a common outlet conduit 94 equipped with a pressure gauge 96. The conduit 94 is connected to a valve 98, the output conduit 100 of which passes through a $7\mu$ filter 102 (Swagelok SS-4FW-7) and leads to a gas booster 104 (Haskell AGD-7, C8 single stage, double acting). The output conduit 106 from booster 104 includes a valve 108, pressure gauge 110, proportional pressure relief valve 112 (Nupro SS-4R3A-E, 2250–3000 psig), flow meter 114 and valves 115, 115a. As shown, the conduit 106 passes into bath 12 and is coupled to the input of surge tank 28.

The solvent recovery system 26 includes, in addition to micrometering valve 64, a heated solvent separation cylinder 116. As shown, a heated output line 118 from the valve 64 includes a thermocouple 119 and leads to the input of cylinder 116, whereas an output line 120, equipped with thermocouple 122 and valve 124, allows recovery of solvent. A gas line 126 extends from the top of cylinder 116 and leads to ¼ inch coiled copper tubing 128. The output 130 from the latter has a thermocouple 132 and leads to a rotameter 134 (Gilmont Accucal GF-4540-1250, 0-126 SLM $CO_2$).

In order to provide further process control, a transducer 136 and pressure gauge 138 are connected via line 140 to a port 141 of chamber 18. Similarly, a transducer 142 and pressure gauge 144 are connected by way of line 146 to conduit 36 as shown. Finally, an observation light 148 is situated exteriorly of the chamber 18 to allow observation of the micronization process through one of the observation ports 150, 151 of the chamber 18.

The operating, control and monitoring components of the apparatus 10 are conventionally connected with a personal computer (not shown). This computer has a known control/data logging program loaded thereon.

This set of experiments was conducted as a $2^3$ factorial design with a center point replicate. The eight experiments were run in random order, followed by the three replicates. The three variables (along with their low and high values) were $CO_2$ pressure (1200 and 1400 psig), solution concentration (15 and 30 mg/mL), and solution flow rate to the nozzle 20 (2 and 4 mL/min). The rationale behind the selected variable ranges is as follows. The low value of the $CO_2$ pressure is above the critical pressure of $CO_2$ (~74 bar), whereas the high value was limited by the output of the gas booster used to pressurize the $CO_2$. This output is constrained by the house air pressure (85 psig) used to drive the booster. The design limitation of the booster is 2500 psig, for an air supply pressure of 150 psig. The selected range of concentrations takes advantage of the high solubility of insulin in HFIP (~40 mg/mL). The solution flow rates are within the design specifications of the nozzle.

The remaining parameters were maintained constant throughout each experiment. Temperature was maintained by the bath 12 at 37° C., and above the critical temperature of $CO_2$ (~31° C.). $CO_2$ mass flow rate was 75 SLM (137 g/min).

The procedure used in all of the separate runs is set forth below.

1. In order to ensure adequate $CO_2$ was present in the cylinders 86, 88 the pressure on gauge 96 upstream of the gas booster 104 was noted. For these dip tube cylinders 86, 88, the pressure remained constant (~900 psig) while liquid $CO_2$ is being withdrawn, then the pressure began to drop. A minimum pressure is required to achieve adequate outlet pressure from the gas booster—a higher outlet pressure (e.g. 1400 psig) requires a higher inlet pressure.

2. The data acquisition and control program was placed in RUN mode. A new file for data logging was opened.

3. The amount of insulin to dissolve in 20 mL HFIP was weighed out, and placed in a 25 mL Erlenmeyer flask with ground glass stopper. A stir bar was added to the flask and 20 mL HFIP directly from the solvent bottle was pipetted into the flask. The stopper was replaced and the joint was sealed with Parafilm. The mixture was stirred at medium setting (4) for at least two hours.

4. The 0.2 $\mu$m PTFE filter was weighed and installed in the filter 16.

5. The precipitation chamber 18, surge tank 28 connected to valves 34, 40 and the parallel filters 14, 16 were placed in the bath 12, and the outlet of the chamber 18 was connected to conduit 46 leading to valve 40. Valves 34, 40 were turned such that valve 34 directed $CO_2$ flow from the surge tank 28 to the inlet of the chamber 18, and valve 40 directed $CO_2$ flow from the outlet of the chamber 18 to the parallel filter system. The two three-way valves 44, 58 of the parallel filter system were turned to direct flow through the 0.2 $\mu$m filter 16.

6. The rest of the tubing and thermocouple connections for the complete setup were then made as described previously and illustrated in FIG. 1. Valve 78 was then turned to isolate the chamber 18 from the syringe pump 72, and the two-way valve 84 that connected valve 78 to the atmosphere was opened. This prevented high pressure $CO_2$ from entering the solution line and syringe pump.

7. The bath 12 was filled with water to a level covering the filters and outlets of the chamber 18 and surge tank 28.

8. Valve 62 was closed and the system was pressurized with $CO_2$ by operating the air drive of gas booster 104. $CO_2$ flowed from the cylinders 86, 88 simultaneously; this maintained $CO_2$ cylinder pressure for a longer period of time, thereby reducing the frequency of adjustments necessary to maintain gas booster outlet $CO_2$ pressure (and thereby chamber 18 pressure) during the runs.

9. If no leaks were present, pressurization was continued with $CO_2$ to the experimental pressure, and the bath 12 was filled with water until the fittings on top of the chamber 18 were covered. The temperature of the water during filling was monitored and controlled, to minimize the time required for the immersion heater to achieve and maintain 37° C.

10. The immersion heater was started to heat the water to the desired temperature. The temperature was checked with an ASTM 38C thermometer. The temperatures of the water bath and $CO_2$ in the chamber 18 were allowed to reach 37° C.

11. The insulin solution was filtered through a 0.2 μm PTFE syringe filter into a 25 mL graduated cylinder. This cylinder was sealed with Parafilm to create the reservoir 22.

12. Valve 62 was opened and micrometering valve 64 was adjusted to achieve a 75–76 SLM $CO_2$ at ±4° C.

13. The program was then used to turn on the heaters: associated with micrometering valve 64, cylinder 116, and transfer line 118.

14. The air drive pressure on the gas booster 104 was adjusted to obtain the downstream, or chamber 18, pressure, as read off the downstream pressure gauge 138. Typically, the gas booster outlet pressure is 40 psi greater than the downstream pressure.

15. The micrometering valve 64 was then adjusted as necessary to obtain a 60 on the scale of the rotameter.

16. The downstream temperature and pressure recorded by thermocouple 70 and transducer 136 were allowed to stabilize, as indicated by graphs displayed on the monitor output.

17. The syringe pump 72 was then filled with 3 mL solvent, and this solvent was pumped into the conduit 74. The initial flow of solvent through the nozzle 21 was designed to prevent plugging of the capillary.

18. The observation light 148 was then turned on.

19. The two-way valve 84 connected to valve 78 was closed, along with the syringe pump outlet valve 72b. The syringe pump 72 was filled with solution, at a flow rate of 20 mL/min. The syringe pump inlet valve 72a was closed and the syringe pump outlet valve 72b was opened. The contents of the syringe pump 72 were pressurized at the desired flow rate (e.g. 2 mL/min) until the syringe pump pressure (as indicated on the pump's display) was greater than the chamber 18 pressure; at this point, the valve 78 was turned to permit flow of the solvent/solution to the nozzle 20.

20. Data logging on the control program was enabled and timing was begun with the stopwatch. This constituted the beginning of a test run.

21. While the solution was flowing through the nozzle 20, the spray and/or particle formation was observed through the window 151.

22. Solution was continually pumped at the desired flow rate until the syringe pump 72 was emptied; at this point the outlet valve 72b was quickly closed. The syringe pump was depressurized, then the syringe pump inlet valve 72a was opened to rapidly fill the syringe pump (20 mL/min) with ~7 mL solvent. The syringe pump inlet valve 72a was closed to pressurize the syringe pump at the experimental flow rate until the syringe pump pressure was greater than the chamber 18 pressure, whereupon the syringe pump outlet valve 72b was opened. This step was designed to flush the remaining solution from the line and from the ~1 mL dead volume in the nozzle 20.

23. Solvent was pumped at the desired flow rate until the syringe pump 72 was emptied, whereupon the outlet valve 72b was closed and the valve 78 was turned to isolate the chamber 18.

24. $CO_2$ was passed continuously through the chamber 18 for a given length of time (e.g., 1.5 h), at least until powder could no longer be seen floating in the chamber 18. Chamber pressure was monitored on the downstream pressure gauge 138 and the control program display, and the inlet pressure (gas booster outlet pressure) was adjusted via the air drive to maintain the chamber pressure, if necessary. The micrometering valve was adjusted to maintain constant pressure.

25. The valves 38, 40 were then turned to direct flow of $CO_2$ from the surge tank 28 directly through the 0.2 μm filter 16, isolating the chamber 18. The 0.2 μm filter was flushed with $CO_2$ for 30 minutes.

26. The outlet from the gas booster 104 was shut off to allow the surge tank 28 to depressurize through the 0.2 μm filter 16, at constant pressure. The immersion heaters were turned off toward the end of depressurization, when the temperatures began to rise.

27. The micrometering valve 64 was closed and the valves 44, 58 were turned to direct flow through the 0.5 μm filter 14, whereupon the valve 40 was turned to direct flow from the chamber 18 outlet 48 to the filter 14.

28. The heaters (except the condenser heater) were turned on and the micrometering valve 64 was opened to in order to depressurize the contents of the chamber 18.

29. The heaters, including the immersion heater, were turned off and data logging was disabled. This is the end of the run.

30. Water was then siphoned from the bath 12 and the tubing and thermocouples were disconnected.

31. The tubing from the outlet 48 of the chamber 18 was disconnected, and the surge tank/valves/parallel filter assembly was removed along with the chamber 18.

32. The lid of the chamber 18 was unscrewed and the lid was carried, with the nozzle attached, to the syringe pump 72.

33. The outlet line 74 from the syringe pump was removed and the pump was filled with 20 mL DMSO. The pump was allowed to sit, giving time for the DMSO to solubilize any insulin remaining in the pump.

34. Helium was blown through the outlet line 74 and attached lid/nozzle, to remove the DMSO.

35. The nozzle from the lid was removed and the nozzle was sonicated in a beaker full of sufficient DMSO to cover the annular resonator cavity and tip of the capillary. The nozzle was rinsed with water and acetone, and dried with helium. The capillary inlet was connected to a helium cylinder to flush the remaining liquid from the capillary.

36. A weigh tray was tared, and powder was collected from the windows using a scoopula, with the powder being placed in the tray. Powder was also collected from the walls of the chamber 18. The collected powder was then weighed and placed in a labeled glass vial under helium. The vial was stored at −20° C.

37. The 0.2 μm filter holder was disassembled and the filter was carefully dislodged and weighed. Using the weight of the PTFE filter, the amount of precipitate collected on the filter was calculated. The powder plus the filter was placed in a labeled glass vial under helium. This vial was also stored at −20° C.

38. The 0.5 μm filter was disassembled and if any powder was collected therein the powder was optionally weighed and stored. The purpose of the 0.5 μm filter was to trap any powder that leaves the chamber during depressurization, rather than to collect significant amounts of product.

A series of tests was performed to characterize the micronized insulin products, both physically and chemically. HPLC and CD were used to characterize the insulin in solution; IR and Raman spectroscopy were used to characterize the insulin in the solid state. Aerosizer and SEM provided particle size distributions and particle morphologies. Thermogravimetric analysis (TGA) determined the level of volatiles in the processed powder.

Three HPLC methods (Potency, Purity and Polymer) were run on the processed insulin powder reconstituted in aqueous solution. The methods gave an indication of the potency of the insulin, the purity and the polymer content. The processed insulin is referred to as PCA (precipitation with compressed antisolvents) insulin.

Tables 1 and 2 summarize the HPLC results. HMWP refers to high-molecular weight polymer. When reconstituted in water, the PCA insulin was as potent as unprocessed insulin, with some slight pressure and concentration factor effects. PCA insulin was also slightly degraded, containing more polymer and insulin related substances. Over the range of variables studied, the experimental factors (pressure, concentration and flow rate) had no significant effect on purity or polymer content of the processed insulin.

TABLE 1

HPLC Results - Effect of PCA on Reconstituted Insulin

| HPLC Method | Measurement | PCA Average | Unprocessed Insulin |
| --- | --- | --- | --- |
| Potency | "as is" Potency (U/mg) | 26.8 | 25.9 |
| Purity | Main Peak Insulin % | 97.9% | 99.1% |
| Polymer | HMWP % | 0.65% | 0.10% |

TABLE 2

HPLC Results - Significant Factor Effects (5% Level)

| Measurement | Main Effect | Interaction |
| --- | --- | --- |
| "as is" Potency (U/mg) | Pressure (+) Concentration (+) | Concentration-Flow rate (−) |
| A21 Desamido Insulin (%) | None | None |
| Other Insulin Related Substances (%) | None | Pressure-Flow rate (+) Concentration-Flow rate (+) |
| HMWP % | None | None |

CD was also performed on the processed insulin, reconstituted in water. FIGS. 3A, 3B, 4A and 4B show the far-UV and near-UV CD spectra of the processed insulin and unprocessed insulin (UPI), respectively. The three numbers for each spectrum of processed insulin (e.g. 1200, 15, 2) represent the factor levels for pressure (1200 psig), concentration (15 mg/mL) and flow rate (2 mL/min). Other than the 1200,15,2 datum, the CD spectra are quite similar, meaning the processed and unprocessed insulins have similar secondary to quaternary structure when reconstituted in water. The anomalous scan of the 1200,15,2 sample in the lower graphs of FIGS. 3B and 4B was due to inaccurate concentration of insulin for this sample. The y-axis scale (mean residue ellipticity, or [Θ]) is obtained by multiplying the angle obtained from the raw CD data by a factor that incorporates the concentration of the sample. This concentration is obtained from a UV absorbance measurement at 280 nm. In the case of the 1200,15,2 sample, some additional component in the sample was absorbing at this frequency, such that the calculated concentration of insulin was greater than the actual concentration in the sample.

Figure 3A:
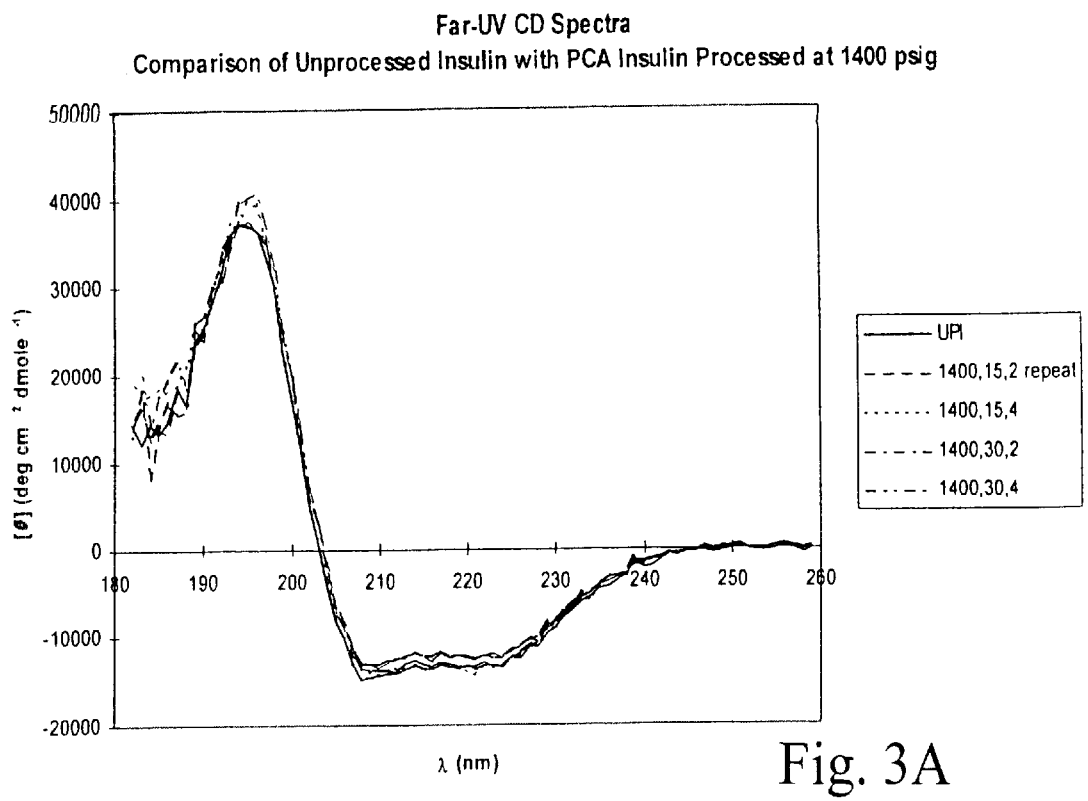
FIG. 3A is a far-UV CD spectra comparing unprocessed insulin with insulin processed in accordance with the invention at a total pressure within the precipitation chamber of 1400 psig, as set forth in Example 1.
Figure 3B:
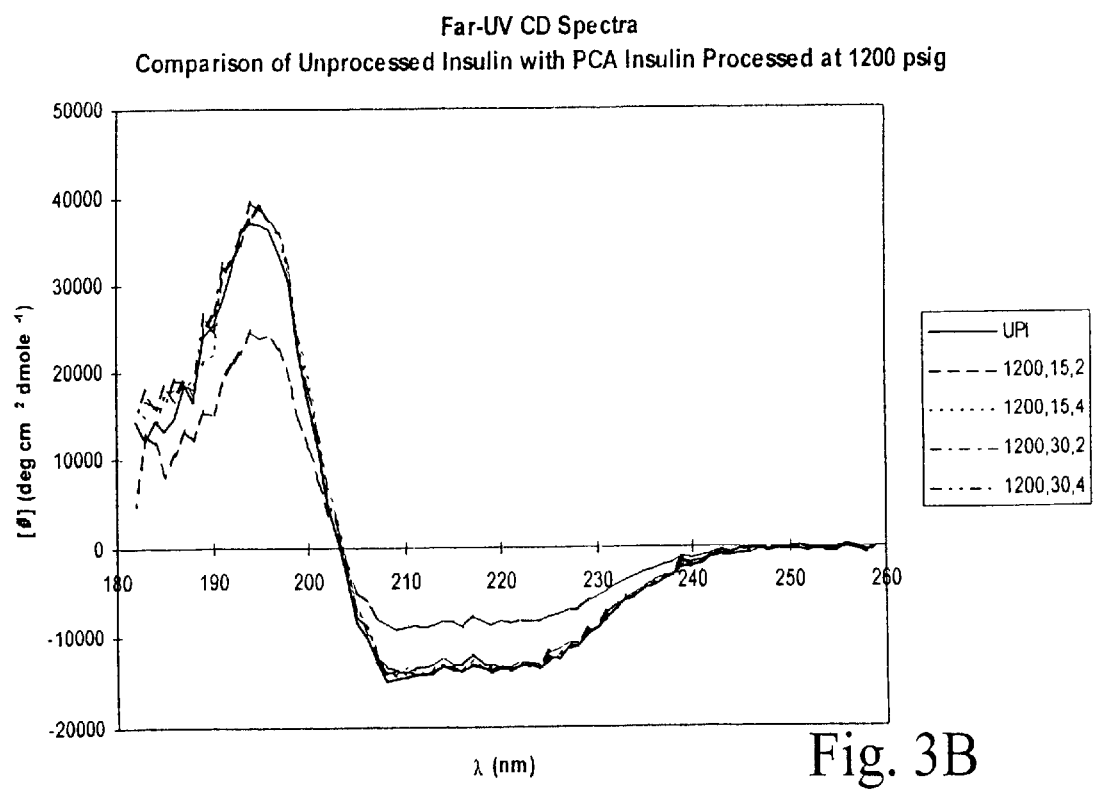
FIG. 3B is a far-UV CD spectra comparing unprocessed insulin with insulin processed in accordance with the invention at a total pressure within the precipitation chamber of 1200 psig as set forth in Example 1.

The secondary structure (α-helix mainly) of the unprocessed insulin is similar to that of the processed insulin, based on the similarity of the far-UV CD spectra (180–260 nm) in FIGS. 3A and 3B. Electronic transitions of the amide chromophore occur in this region. The amide forms the peptide bond in the backbone of the protein, and its CD absorbance is influenced by secondary structure.

Figure 4A:
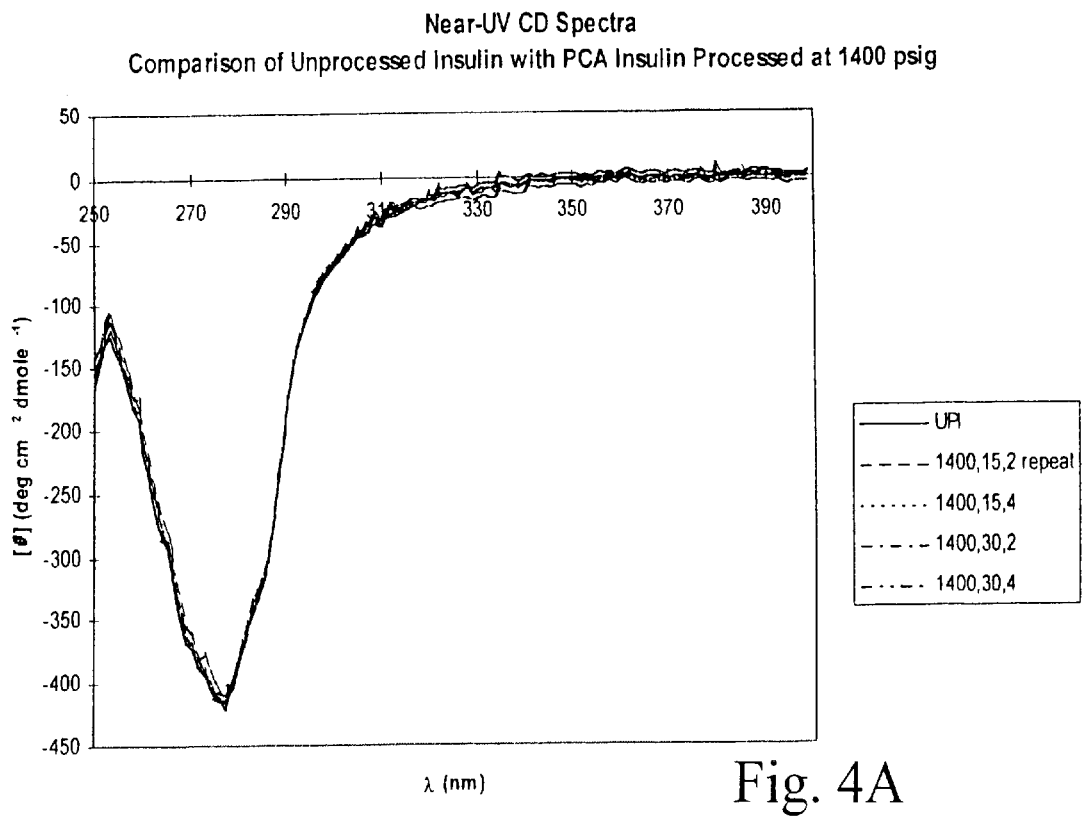
FIG. 4A is a near-UV CD spectra comparing unprocessed insulin with insulin processed in accordance with the invention at a total pressure within the precipitation chamber of 1400 psig as set forth in Example 1.
Figure 4B:
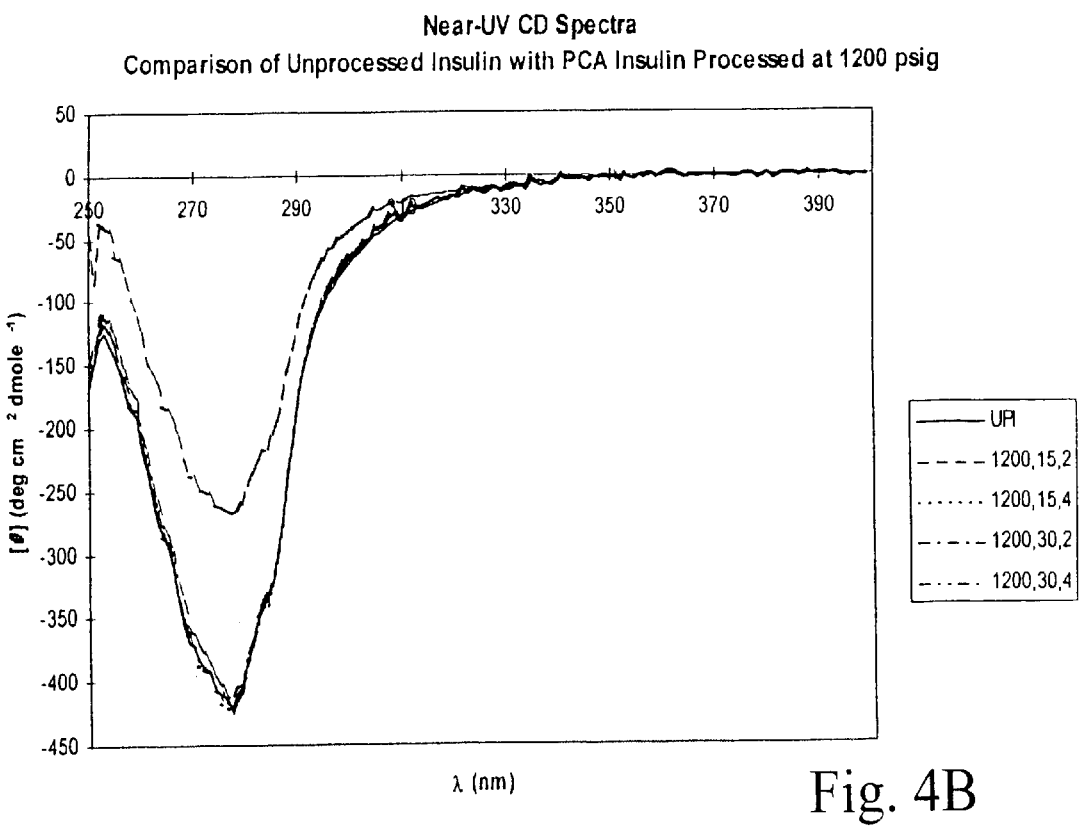
FIG. 4B is a near-UV CD spectra comparing unprocessed insulin with insulin processed in accordance with the invention at a total pressure within the precipitation chamber of 1200 psig as set forth in Example 1.

The tertiary/quaternary structure of the unprocessed insulin is similar to that of the processed insulin. based on the similarity of the near-UV CD spectra (250–400 nm) in FIGS. 4A and 4B. Electronic transition of the tryosine chromophore occurs in this region. There are four tyrosine amino acid residues in the insulin molecule (monomer). The folding of the monomer (tertiary structure) and association with other monomers (quaternary structure) influence the CD absorbance of these residues. The unprocessed insulin contains zinc, and exists as a hexamer (non-covalent aggregate of six monomers) in solution at neutral pH. The similar near-UV CD spectra suggest the processed insulin contains hexameric material as well.

In summary, CD demonstrated that the PCA process does not significantly affect the structure of insulin when reconstituted in aqueous solution. In addition, qualitatively there is little difference among the experimental treatments, over the range of pressure, concentration and flow rate studied.

CD was also performed on unprocessed insulin dissolved in both water and HFIP. The far-UV spectra indicate some secondary structural changes in HFIP. The near-UV spectra point to unfolding and dissociation of the insulin hexamer into monomers in HFIP. Hence, dissolution of insulin in HFIP appears to change the structure of insulin; however, these changes are reversible.

IR and Raman spectroscopy were used to determine the solid-state structure of the processed insulin powder, collected from both the filter 16 and the precipitation chamber. IR was conducted using a Nicolet Nic-Plan IR™ microscope connected to a Nicolet Magna-IR 850 Spectrometer Series II.

In each IR spectroscopy case, based on a qualitative comparison of the spectra with that of native insulin, little difference was observed among treatments and the Fourier Self-Deconvoluted (FSD) spectra were similar to that of native insulin. However, the data suggested a higher sheet content and some denaturation for PCA insulin. Each FSD spectra was integrated and factorial analyses were run on both the helix and sheet content, for filter and chamber product. In all cases, there were no significant factors or interactions.

For Raman spectroscopy, a Nicolet Raman 950 spectrometer was used, along with OMNIC 4.1a software. Samples were pelletized by compression in a hydraulic press and the cylindrical pellets were placed in a sample holder for scanning. Laser power was limited to 250 mW, to avoid burning the samples. For each sample, 6000 scans were taken.

These analyses allowed some conclusions to be drawn about the solid-state structure of the PCA insulin. Qualitatively, both IR and Raman indicate that the PCA product contains less α-helix than native insulin, but the amount of degradation is not large. A comparison of spectra shows that Raman spectroscopy is a more sensitive technique than IR for detecting structural differences in insulin. Note the spike in the Raman spectrum for insulin fibrils, corresponding to β-sheet. This discrepancy may be the inaccurate method of quantifying relative structural content.

Particle size distributions (PSD) and morphology were determined using Aerosizer and SEM. For the Aerosizer, the true density of insulin crystals from Lilly Lot No. 002LX9 (density=1.30) was used as input. This density should be the same for Lot No. 009LX9 assuming the two lots have the same crystal form. The Aerosizer results are summarized in Table 3.

TABLE 3

PSD Results from Aerosizer for PCA Insulin

| Collection | Distribution | Mean Dia. | S.D. | 10% Under | 50% Under | 90% Under |
| --- | --- | --- | --- | --- | --- | --- |
| Filter | Number | 1.87 | 1.69 | 1.05 | 1.71 | 3.85 |
|  | Volume | 6.90 | 1.83 | 2.88 | 7.82 | 13.79 |
|  | $d_V/d_N$ | 3.68 |  |  |  |  |
| Chamber | Number | 0.97 | 1.67 | 0.55 | 0.92 | 2.35 |
|  | Volume | 4.22 | 1.99 | 2.26 | 4.18 | 9.03 |
|  | $d_V/d_N$ | 4.37 |  |  |  |  |

As seen in Table 3, both number and volume distributions are narrow, and the mean diameter of the number distribution falls within the 1–5 micron range suitable for pulmonary delivery.

SEM was run on the three of the PCA insulin samples. The samples were prepared under different conditions, and were examined for particle morphology, size uniformity, and the occurrence of aggregation. Examination of the powder by SEM revealed that the particles have a fibrous matrix structure.

The PCA samples were also analyzed by TGA (25–195° C.), giving a PCA powder volatile content of from 3–6% probably due to moisture absorbed from the atmosphere.

EXAMPLE 2

In this example albumin samples dissolved in HFIP were recrystallized using the invention. The resultant particulate albumin was characterized by Aerosizer and SEM.

The apparatus used in this example is identical to that described in Example 1 and depicted in FIG. 1, except that a filter (55-6TF-7, 0.5 μm) was used in lieu of the parallel filter assembly 14, 16 of FIG. 1. A similar procedure recited in Example 1 was used in these experiments.

The albumin samples (Sigma Chemical Co., Lot 29H0684) were dissolved in HFIP at concentrations ranging from 25–30 mg/mL. The nozzle spray rate was 2 mL/min. The $CO_2$ flow rate was 75 sL/min. (0.161 kg/min.). In each experiment about 24–35 mL of albumin solution was sprayed into the chamber 18. The recrystallized samples were characterized by CD to determine any alteration in the conformation of the precipitated samples as compared with the starting albumin, by Aerosizer particle size analyzer (Amherst Process Instruments, Inc.) to determine particle size and size distribution, and by SEM (HITACHI, S-570) to determine the particle size and morphology.

The following Table 4 shows the experimental results (harvested particle amounts and recovery yields) and Aerosizer analysis results for the albumin samples. Micron-size particles were obtained with reproducible yield and particle size distribution. All the samples contained very few particles below 0.7 μm (about 10% or less). A large number of particles were found to be very near to 2 μm. Most experiments produced particles which had a single (unimodal) population distribution. The recovery yield was about 57%, with the majority of particles harvested from the external filter.

Figure 5:
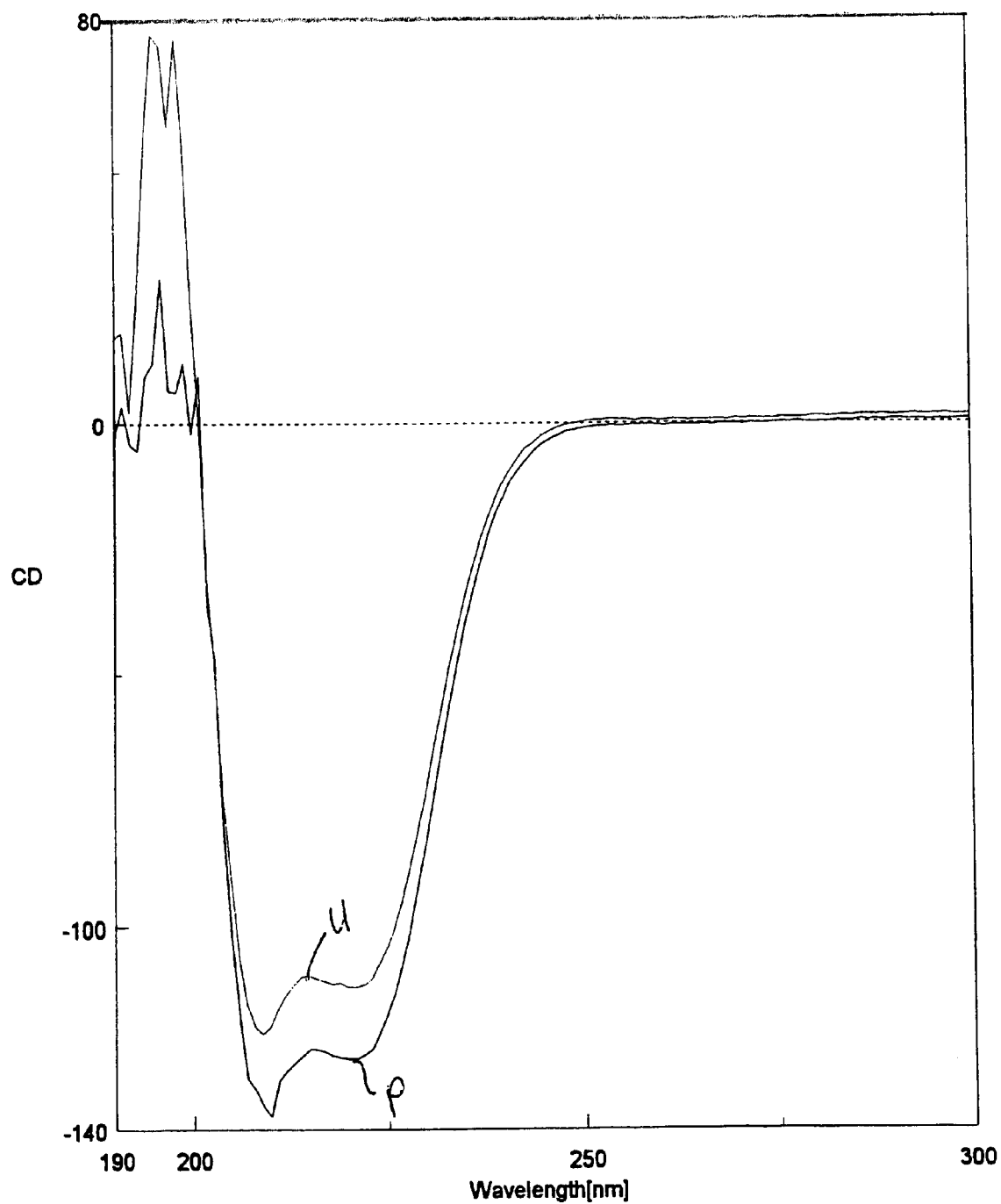
FIG. 5 is a CD spectra of unprocessed (U) and processed (P) albumin from Example 2.
Figure 6:
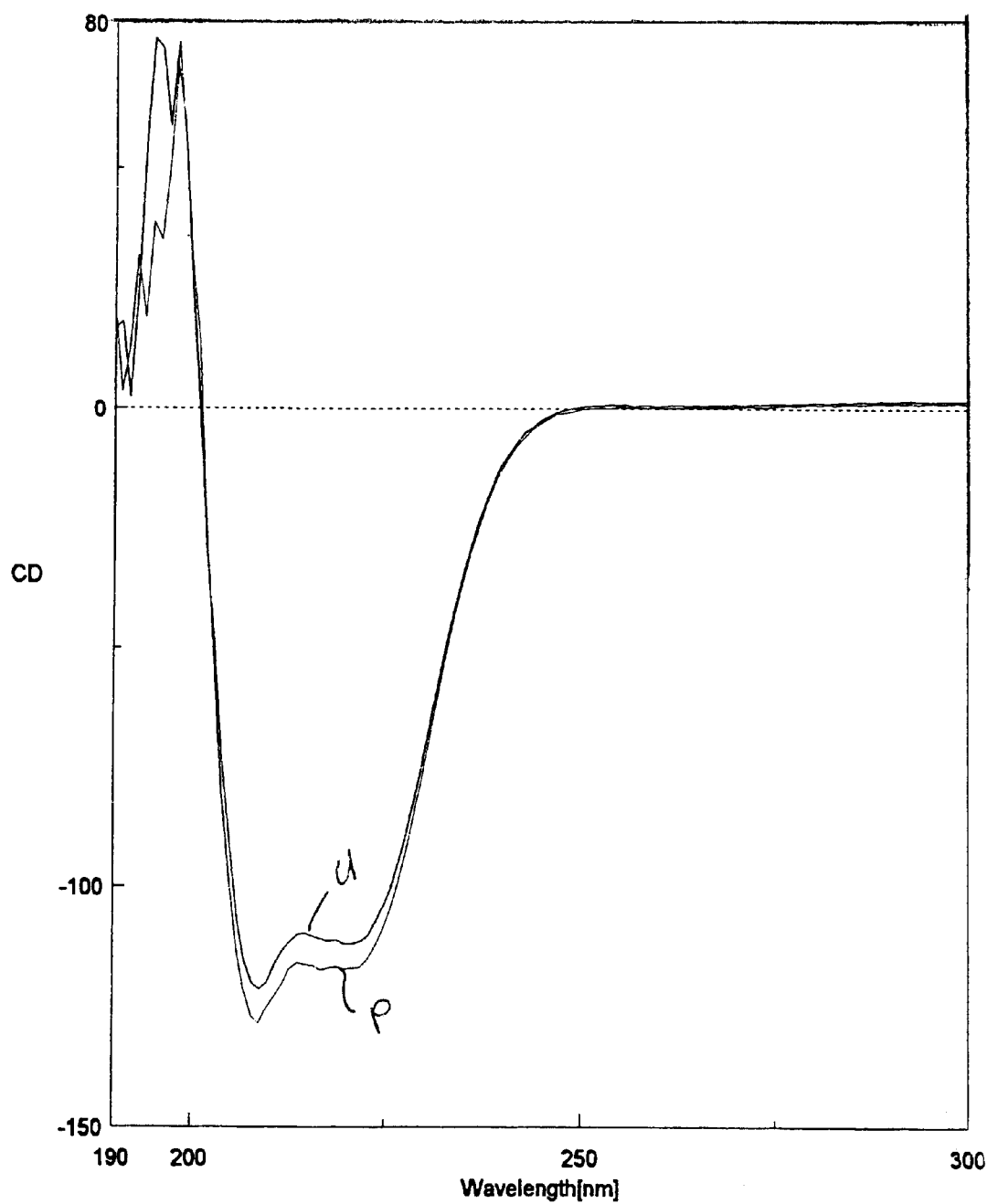
FIG. 6 is a CD spectra of unprocessed (U) and processed (P) albumin from Example 2.

The CD scans of both unprocessed and processed albumin samples were very similar, indicating that there was no significant change in the protein conformation and the precipitated particles could attain native protein conformation. FIGS. 5 and 6 are representative spectra of processed (P) and unprocessed (U) albumin obtained from the precipitation chamber and the filter, respectively. Differences in intensity result from differences in protein concentrations.

SEM analysis of the samples of unprocessed and processed albumin under different magnifications (20 and 100μ) demonstrates that the particle size of processed albumin samples is much smaller than unprocessed samples.

We claim:

1. A method of forming small protein particles comprising the step of contacting a protein, a solvent system for the protein, and an antisolvent for the protein solvent system under conditions to at least partially dissolve the protein solvent system in the antisolvent with consequent precipitation of the protein, at least a part of said protein solvent system being a halogenated organic alcohol.

2. The method of claim 1, said solvent system consisting essentially of a single halogenated organic alcohol.

3. The method of claim 1, said alcohol being a halogenated alkyl alcohol.

4. The method of claim 3, said alcohol being a halogenated $C_{1-C4}$ alkyl alcohol.

5. The method of claim 4, said alcohol selected from the group consisting of 1,1,1,3,3,3-hexafluoro-2-propanol, trifluoroethanol, 2-chloroethanol and mixtures thereof.

6. The method of claim 5, said alcohol being 1,1,1,3,3,3-hexafluoro-2-propanol.

7. The method of claim 1, said antisolvent selected from the group consisting of $CO_2$, propane, butane, isobutane, nitrous oxide, sulfur hexafluoride, trifluoromethane, hydrogen and mixtures thereof.

8. The method of claim 7, said antisolvent being $CO_2$.

9. The method of claim 1, the contact between said protein, solvent system and antisolvent being carried out at near or supercritical conditions for the antisolvent.

10. The method of claim 9, said conditions being about 0.5–2 $P_c$ and about 60° C.

11. The method of claim 10, said conditions being about 0.9–1.5 $P_c$ and about 50° C.

12. The method of claim 1, further comprising the step of first forming a solution of said protein and said protein solvent system, and then contacting droplets of said solution with said antisolvent under conditions to precipitate said small protein particles.

TABLE 4

| | Flow Rate | | Particle size (μm) by Aerosizer analysis | | | | | |
| | | | Number distribution | | | Volume distribution | | |
| Run | SL/min | Other conditions | Mean | 10% | 95% | Mean | 10% | 95% |
| 1 | 75 | 30.0 mg/mL, 35 mL, 2.0 mL/min, ultrasonic nozzle | 1.30 | 0.55 | 5.91 | 9.23 | 4.40 | 16.1 |
| 2 | 75 | 25.0 mg/mL, 35 mL, 2.0 mL/min, ultrasonic nozzle | 1.48 | 0.73 | 5.91 | 11.1 | 5.13 | 19.3 |
| | | | | | Not Analyzed | | | |
| 3 | 75 | 25.0 mg/mL, 23.9 mL, 2.0 mL/min, ultrasonic nozzle | 1.42 | 0.66 | 5.31 | 11.4 | 4.97 | 19.7 |
| | | | 1.37 | 0.64 | 5.37 | 9.39 | 4.49 | 15.7 |
| 4 | 75 | 25.0 mg/mL, 27 mL, 2.0 mL/min, ultrasonic nozzle | 1.96 | 0.56 | 10.4 | 12.8 | 6.24 | 21.0 |
| | | | 2.88 | 1.11 | 11.8 | 12.7 | 6.12 | 20.5 |

• V indicates precipitation vessel or chamber 18; F indicates filter
• The data of the first row in particle size for every run are from vessel sample.
• The data of the second row in particle size for every run are from filter sample.

13. The method of claim 12, further comprising the step of spraying said solution through a nozzle into a zone containing said antisolvent.

14. The method of claim 12, said contacting step being carried out within a precipitation chamber, the total pressure within said chamber being from about 0.5–2 $P_c$ of the gas within said chamber.

15. The method of claim 14, said pressure being about 0.9–1.5 $P_c$.

16. The method of claim 1, said antisolvent being $CO_2$, said total pressure being from about 1000–2000 psig.

* * * * *